United States Patent [19]

Lee

[11] 4,011,860

[45] Mar. 15, 1977

[54] CALIBRATED BLOOD PRESSURE MEASURING SYSTEM AND METHOD

[75] Inventor: John J. Lee, Cupertino, Calif.

[73] Assignee: Filac Corporation, Sunnyvale, Calif.

[22] Filed: Oct. 20, 1975

[21] Appl. No.: 623,719

[52] U.S. Cl. .................. 128/2.05 M; 128/2.05 A
[51] Int. Cl.² ........................................ A61B 5/02
[58] Field of Search ............ 128/2.05 A, 2.05 M, 128/2.05 C, 2.05 G, 2.05 R

[56] References Cited

UNITED STATES PATENTS

| | | | |
|---|---|---|---|
| 3,894,535 | 7/1975 | Cannon et al. | 128/2.05 A |
| 3,905,353 | 9/1975 | Lichowsky | 128/2.05 M |
| 3,905,354 | 9/1975 | Lichowsky | 128/2.05 M |

Primary Examiner—Robert W. Michell
Assistant Examiner—Lee S. Cohen
Attorney, Agent, or Firm—Flehr, Hohbach, Test, Albritton & Herbert

[57] ABSTRACT

Blood pressure measuring system and method in which the pressure transducer connected to an occluding cuff is isolated from the pressure source provided for inflating the cuff and a reference pressure is maintained in the transducer during a calibration cycle at the outset of a blood pressure measurement. During the calibration cycle, the level of the output signal provided by the transducer is adjusted until a reference level is reached, and thereafter the transducer is reconnected to the pressure source for the blood pressure measurement.

8 Claims, 2 Drawing Figures

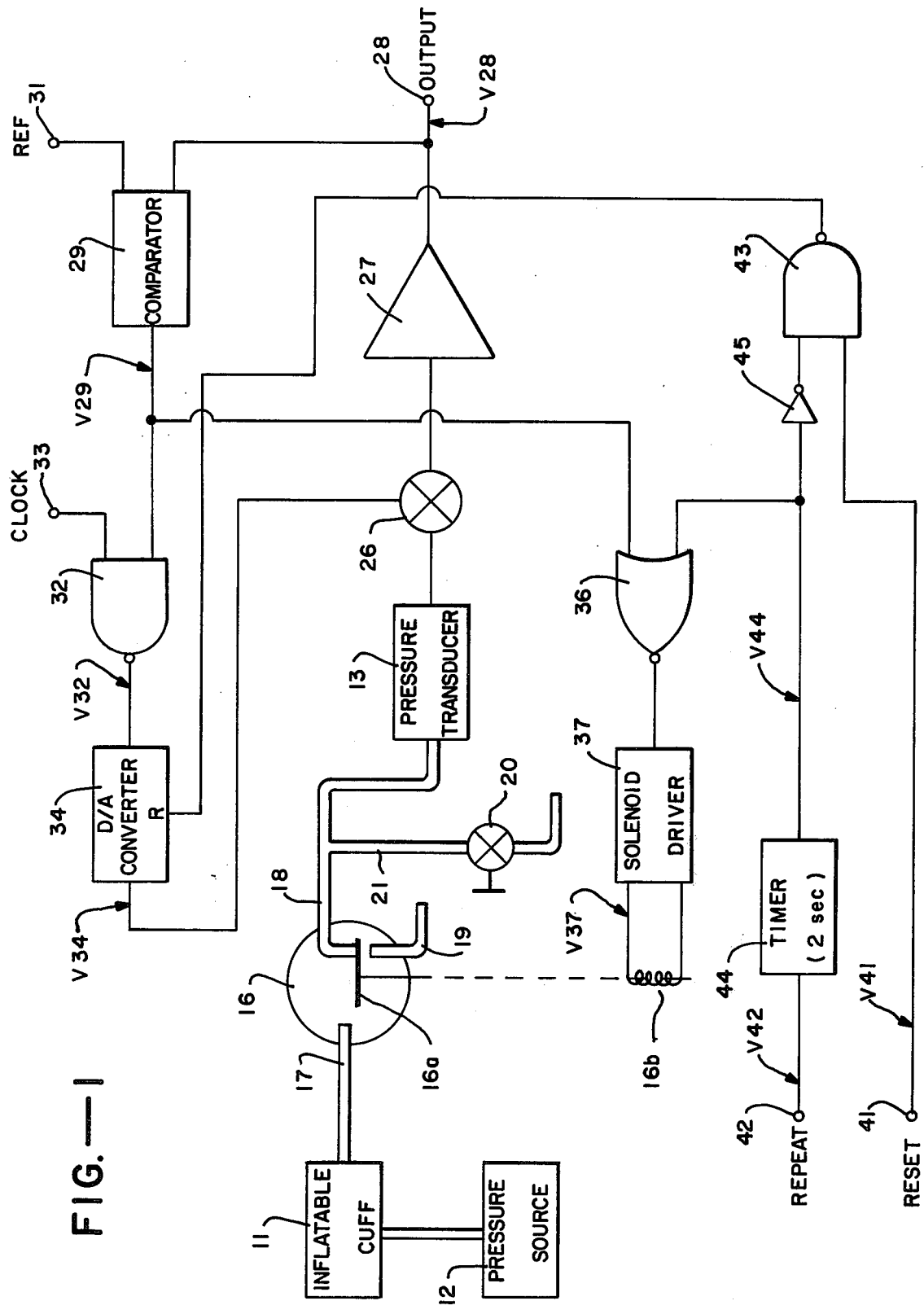
FIG.—1

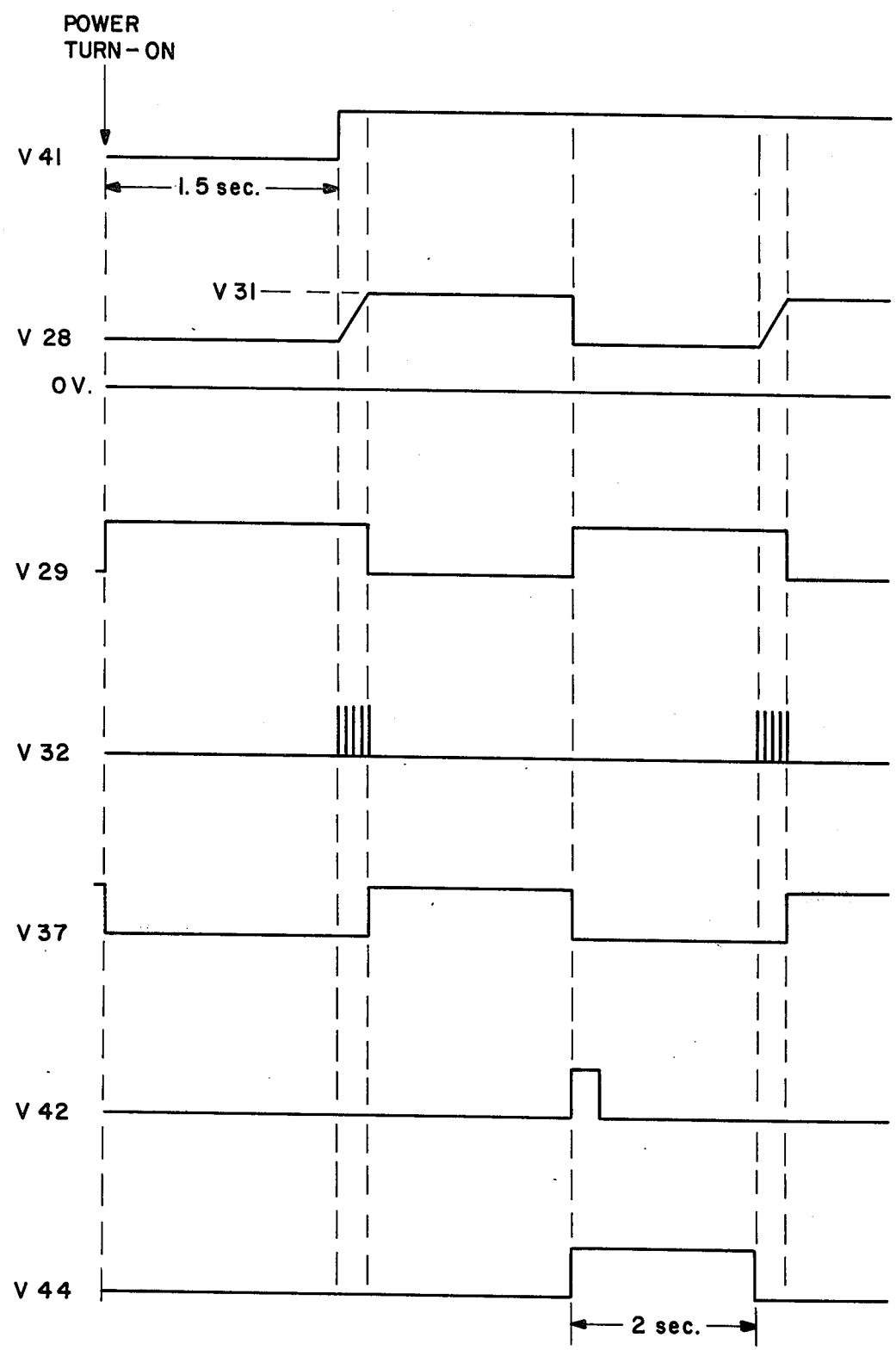
FIG.—2

4,011,860

CALIBRATED BLOOD PRESSURE MEASURING SYSTEM AND METHOD

BACKGROUND OF THE INVENTION

The invention pertains generally to blood pressure measuring apparatus and more particularly to a system and method for calibrating a blood pressure measuring system.

Due to problems of temperature sensitivity and zero point drift encountered with pressure transducers, particularly semiconductor transducers, utilized in blood pressure measuring systems of the type disclosed, for example, in co-pending application Ser. No. 539,799, filed Jan. 9, 1975, now U.S. Pat. No. 3,978,848 and assigned to the assignee herein, it is generally advisable to recalibrate or rezero such systems at the outset of each measurement. In non-invasive systems in which the brachial artery is occluded by an inflatable cuff, a further problem exists in that residual air in the inflation bag or premature application of pressure can produce a significant error during calibration.

SUMMARY AND OBJECTS OF THE INVENTION

In the system and method of the invention, the pressure transducer of the blood pressure measuring system is isolated from the pressure source provided for inflating the cuff during a recalibration cycle at the outset of each blood pressure measurement. During the recalibration cycle, a reference pressure is maintained in the transducer and the level of the output signal is adjusted until a reference level is reached. At the conclusion of the calibration cycle, the transducer is reconnected to the pressure source for the blood pressure measurement.

It is in general an object of the invention to provide a new and improved blood pressure measuring system and method.

Another object of the invention is to provide a system and method of the above character in which accurate recalibration or rezeroing is provided at the outset of a blood pressure measurement.

Another object of the invention is to provide a system and method of the above character in which the pressure transducer is isolated from the pressure source and an accurate reference pressure is maintained in the transducer during the recalibration or rezeroing cycle.

Additional objects and features of the invention will be apparent from the following description in which the preferred embodiments are set forth in detail in conjunction with the accompanying drawings.

BRIEF DESCRIPTION OF THE DRAWINGS

FIG. 1 is a block diagram of one embodiment of a blood pressure measuring system incorporating the invention.

FIG. 2 is a timing diagram illustrating the operation of the embodiment shown in FIG. 1.

DESCRIPTION OF THE PREFERRED EMBODIMENTS

As illustrated in FIG. 1, the blood pressure measuring system includes an inflatable cuff 11 of suitable known design adapted to be wrapped about the arm of a patient for occluding the brachial artery. The cuff is inflated with pressurized air from a suitable source 12, such as an inflation bulb, and during blood pressure measurements, the pressure in the cuff is monitored by a pressure transducer 13 which provides an electrical signal corresponding to the air pressure in the cuff. The transducer can be of suitable known design, such as a National Semiconductor model LX1601G.

Communication between source 12 and cuff 11 and transducer 13 is controlled by a solenoid operated valve 16 having an inlet port 17 connected to the pressure source and cuff, an outlet port 18 connected to the transducer, and a port 19 vented to the atmosphere. A valve member 16a selectively blocks either port 18 or port 19, depending upon the energization of an operating coil 16b. In the embodiment illustrated, port 18 is normally closed, and port 19 is normally open. Thus, when the coil is deenergized, the pressure source is vented to the atmosphere through port 19, and when the coil is energized, the pressure source and cuff are connected to the transducer through port 18.

A needle valve 20 is connected to the outlet of valve 16 by a line 21 and provides means for bleeding air through an adjustable orifice to the surrounding atmosphere.

Means is provided for combining the signal from transducer 13 with a calibration signal, comparing the combined signal with a reference signal, and adjusting the calibration signal to calibrate or zero the system. This means includes a summation network 26 having a first input connected to the output of the transducer, the output of the summation network being connected to the input of an amplifier 27. The output of the amplifier is connected to an output terminal 28 and to one input of a voltage comparator 29. A reference voltage of suitable level, such as 1 volt, is applied to a second input of the comparator through an input terminal 31. The output of the comparator is connected to one input of a NAND gate 32, and clock pulses of suitable frequency, e.g. 1 Khz, are applied to a second input of gate 32 through an input terminal 33. The output of the gate is connected to the input of a digital-to-analog converter 34, and the output of the converter is connected to a second input of summation network 26. In the preferred embodiment, the digital-to-analog converter comprises a digital counter having a resistance ladder network connected to the outputs thereof, and the summation network delivers a signal to amplifier 27 corresponding to the sum of the signal from transducer 13 and the signal from converter 34.

The output of comparator 29 is also connected to one input of NOR gate 36, and the output of this gate is connected to the control input of a solenoid driver 37. The solenoid driver is connected to operating coil 16b of valve 16 for energizing the same.

Inputs 41, 42 are provided for receiving input control signals which initiate preparation of the system for blood pressure measurements. In the preferred embodiment, input terminal 41 is adapted to receive a RESET signal when the power supply for the system is first energized. This signal is applied to one input of a NAND gate 43, and the output of this gate is connected to a reset input of digital-to-analog converter 34. Input terminal 42 is adapted to receive a REPEAT signal when a measurement is to be repeated or a new measurement is to be made. This signal is applied to second inputs of NOR gate 36 and NAND gate 43 by a timer 44 which provides a delay of predetermined duration, e.g. 2 seconds, to allow time for residual pressure in the system to bleed off at the outset of the measurement. The connection between the output of timer 44 and the second input of NAND gate 43 is made through an inverter 45. The REPEAT signal can, for example, be provided by momentary closure of a manually operable switch (not shown).

Operation and use of the blood pressure measuring system, and therein the method of the invention, can be described with reference to FIG. 2. It is assumed that the system is connected to a suitable power supply and that a RESET signal V41 is applied to input terminal 41. As illustrated, this signal comprises a 1.5 second negative pulse which occurs when the power supply is first turned on. The RESET signal is applied to the reset input of digital-to-analog converter 34 through NAND gate 43, resetting the converter to an initial level at which it remains until the RESET pulse is removed. Resetting the converter lowers the output voltage V28 to a level below the level of reference voltage V31, causing comparator 29 to deliver an enabling signal V29 to clock gate 32. This signal is also applied to solenoid gate 36 and prevents energization of solenoid coil 16b.

With the solenoid deenergized, valve member 16a blocks port 18, thereby isolating transducer 13 from cuff 11 and pressure source 12. With port 18 blocked, transducer 13 communicates with the surrounding atmosphere through needle valve 20, and the atmospheric pressure is applied to the transducer as a reference pressure. Any residual pressure in cuff 11 or premature pressure from pressure source 12 is vented to the atmosphere through valve port 19.

At the termination of RESET pulse V41, the signal V34 at the output of digital-to-analog converter begins to rise in response to clock pulses V32, producing a corresponding rise in output signal V28. When the level of the output signal reaches the level of the reference signal applied to input terminal 31, comparator 29 switches, disabling clock gate 32 and conditioning gate 36 for energization of the solenoid coil. With coil 16b energized, pressure source 12 and cuff 11 communicate with transducer 13, and the blood pressure measurement can be made in the usual manner.

To repeat a blood pressure measurement, a REPEAT signal V42 is applied to input terminal 42. This signal triggers timer 44, and after a 2-second delay, the timer delivers a reset signal V44 to NAND gate 43 through inverter 45 and to solenoid gate 36. The signal from timer 44 resets converter 34, thereby reducing the level of output voltage V28 below the level of reference voltage V31, whereupon comparator 29 delivers an enabling signal to clock gate 32 and a disabling signal to solenoid gate 36. With solenoid coil 16b deenergized, transducer 13 is again isolated from pressure source cuff 11 and 12, and the pressure within the transducer returns to the ambient reference level. The 2-second delay provided by timer 44 assures adequate time for any previous pressure at the input of the transducer to bleed off through needle valve 20.

Upon termination of the 2-second delay, the output of converter 34 again begins to rise in response to clock pulses V32, and output signal V28 increases accordingly. When the output signal reaches the level of the reference signal, comparator 29 switches, delivering a disabling signal to clock gate 32 and an enabling signal to solenoid gate 36. The solenoid coil is thus reenergized, and pressure source 12 and cuff 11 are reconnected to transducer 13 for the blood pressure measurement.

The invention has a number of important features and advantages. By isolating the pressure transducer from the pressure source and cuff during the calibration or rezeroing cycle, inaccuracies due to residual pressure in the cuff or premature pressure from the source are eliminated. The transducer is connected to an accurate reference pressure, and a stable calibration signal is provided by the digital-to-analog converter.

It is apparent from the foregoing that a new and improved system and method for calibrating a blood pressure measuring system has been provided. While only preferred embodiments have been described, as will be apparent to those familiar with the art, certain changes and modifications can be made without departing from the scope of the invention as defined by the following claims.

What is claimed is:

1. In a blood pressure measuring system of the type having an inflatable cuff for occluding the flow of blood in a portion of the circulatory system of a patient, a pressure source connected to the cuff for delivering air to the cuff to inflate the same, and transducer means connected to the cuff for delivering an output signal corresponding to the pressure in the cuff, the improvement comprising: valve means connected between the cuff and the transducer means for controlling communication between the cuff and the transducer means, means for conditioning the valve means to disconnect the transducer means from the cuff at the outset of a blood pressure measurement, a reference signal source, means for changing the level of the output signal to calibrate the system at the outset of the measurement, and means for comparing the output signal with the reference signal and conditioning the valve means to reconnect the transducer means to the cuff when the output signal reaches a predetermined level relative to the reference signal.

2. The blood pressure measuring system of claim 1 wherein the valve means comprises a solenoid operated valve having a first port connected to the cuff, a second port vented to the atmosphere, and a third port connected to the transducer means.

3. The blood pressure measuring system of claim 1 wherein the means for changing the level of the output signal comprises a calibration signal source and means for adding the calibration signal to the output signal.

4. The blood pressure measuring system of claim 3 wherein the calibration signal source comprises a source of clock pulses, digital-to-analog converter means responsive to the clock pulses for providing an analog calibration signal corresponding to the number of pulses applied thereto, and gate means for passing pulses from the clock source to the converter means until the output signal reaches the predetermined level and thereafter inhibiting the passage of pulses whereby the calibration signal remains at a constant level during the measurement.

5. The blood pressure measuring apparatus of claim 1 further including means for applying a control signal to the means for conditioning the valve means and to the means for changing the level of the output signal to initiate the measurement.

6. The blood pressure measuring system of claim 5 further including means for delivering a reset signal and timing means responsive to the reset signal for delivering the control signal a predetermined time after delivery of the reset signal.

7. In a method for calibrating a blood pressure measuring system comprising an inflatable cuff for occluding the flow of blood in a portion of the circulatory system of a patient, a pressure source connected to the cuff for delivering air to the cuff to inflate the same, and a transducer connected to the cuff for delivering an output signal corresponding to the air pressure in the cuff, the steps of: disconnecting the transducer from the cuff and establishing a reference pressure in the transducer at the outset of a blood pressure measurement, comparing the output signal with a reference signal, adjusting the level of the output signal in discrete increments until the output signal reaches a predetermined level relative to the reference signal, and reconnecting the transducer to the cuff when the output signal reaches the predetermined level.

8. The method of claim 7 wherein the level of the output signal is adjusted by providing clock pulses at a predetermined rate, applying the clock pulses to a digital-to-analog converter, adding the output of the converter to the output signal, and inhibiting passage of further clock pulses to the converter when the output signal reaches the predetermined level.

* * * * *